US012594226B2

(12) United States Patent
Fujino et al.

(10) Patent No.: US 12,594,226 B2
(45) Date of Patent: Apr. 7, 2026

(54) METHOD FOR PROMOTING COLLAGEN PRODUCTION

(71) Applicant: Institute of Rheological Function of Food Co., Ltd., Fukuoka (JP)

(72) Inventors: Takehiko Fujino, Fukuoka (JP); Shiro Mawatari, Fukuoka (JP); Masanori Honsho, Fukuoka (JP)

(73) Assignee: INSTITUTE OF RHEOLOGICAL FUNCTION OF FOOD CO., LTD., Fukuoka (JP)

( * ) Notice: Subject to any disclaimer, the term of this patent is extended or adjusted under 35 U.S.C. 154(b) by 595 days.

(21) Appl. No.: 18/010,604

(22) PCT Filed: Jun. 28, 2021

(86) PCT No.: PCT/JP2021/024298
§ 371 (c)(1),
(2) Date: Dec. 15, 2022

(87) PCT Pub. No.: WO2022/004631
PCT Pub. Date: Jan. 6, 2022

(65) Prior Publication Data
US 2023/0293415 A1     Sep. 21, 2023

(30) Foreign Application Priority Data

Jun. 30, 2020    (JP) ................................. 2020-113074

(51) Int. Cl.
*A61Q 19/00*      (2006.01)
*A61K 8/55*       (2006.01)
*A61Q 19/08*      (2006.01)

(52) U.S. Cl.
CPC ............ *A61K 8/553* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 8,236,978 B2 * | 8/2012 | Fujino ...................... | C11B 1/10 |
| | | | 554/20 |
| 8,524,282 B2 * | 9/2013 | Nadachi ................... | A23J 7/00 |
| | | | 554/80 |
| 8,765,169 B2 * | 7/2014 | Kemp ................. | A61L 27/3895 |
| | | | 424/443 |
| 2002/0009509 A1 * | 1/2002 | Bombardelli ........... | A61P 17/00 |
| | | | 514/23 |

FOREIGN PATENT DOCUMENTS

| | | | | |
|---|---|---|---|---|
| CN | 106420558 A | 2/2017 | | |
| JP | 2006-232967 A | 9/2006 | | |
| JP | 2010-063406 A | 3/2010 | | |
| JP | 2019-140919 A | 8/2019 | | |
| JP | 2019-162042 A | 9/2019 | | |
| WO | WO2009/028220 A1 * | 3/2009 | ........... | A61K 31/683 |

OTHER PUBLICATIONS

ISR for PCT/JP2021/024298, dated Aug. 10, 2021.
Fujino et al., "Efficacy and Blood Plasmalogen Changes by Oral Administration of Plasmalogen in Patients with Mild Alzheimer's Disease and Mild Cognitive Impairment: A Multicenter, Randomized, Double-blind, Placebo-controlled Trial", EBioMedicine, 17:199-205 (2017).

* cited by examiner

*Primary Examiner* — Brian J Davis
(74) *Attorney, Agent, or Firm* — GREENBLUM & BERNSTEIN, P.L.C.

(57) ABSTRACT

A method for promoting collagen production, which includes administering to a human a composition containing plasmalogen. The plasmalogen can be a plasmalogen extracted from animal tissues. The composition containing the plasmalogen can be administered to the human as an oral agent or as a parenteral agent. Parenteral agents include external agent and injection agents.

3 Claims, 3 Drawing Sheets

Fig. 5
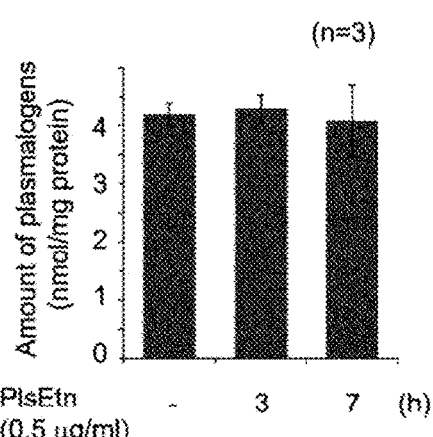
PlsEtn          -          3          7          (h)
(0.5 μg/ml)
Fig. 6
■ C16:0
▨ C18:0
□ C18:1
(n=3)
Amount of plasmalogens (nmol/mg protein)
PlsEtn          -          3          7          (h)
(0.5 μg/ml)
Fig. 7
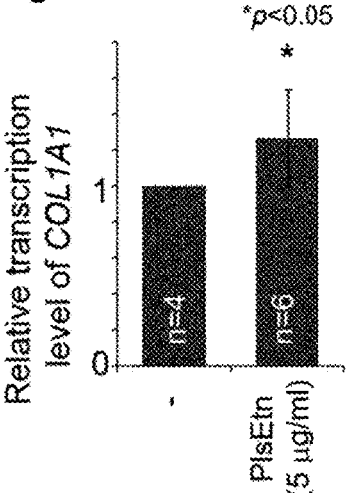

METHOD FOR PROMOTING COLLAGEN PRODUCTION

TECHNICAL FIELD

The present invention relates to a composition that promotes collagen production of skin, to prompt amelioration of skin condition.

BACKGROUND ART

Plasmalogen is one type of phospholipid having an anti-oxidant effect, and is one of glycerophospholipid. Plasmalogen is present in all tissues of mammals, and represents about 18% of phospholipid in human body. However, it is known to be particularly abundant in cranial nerve, cardiac muscle, skeletal muscle, leucocytes, and sperm.

Plasmalogen is known for its action of promoting neurogenesis, action of suppressing nerve inflammation due to lipopolysaccharides (LPS), action of suppressing accumulation of amyloid β (Aβ) protein in brain, etc., and it is said to have effect on cranial nerve disorders such as Alzheimer's disease, Parkinson's disease, depression, and schizophrenia. For example, in non-patent reference 1, it is reported that in patients having orally administered scallop derived-purified plasmalogen, memory function of mild Alzheimer's disease are ameliorated.

On the other hand, collagen in one of proteins that constitute dermis of skin or bones, etc. and represents about 30% of the whole protein in the body. Stromal components being main component of dermis, are mainly constituted by type I and type II collagens. Particularly, type I collagen is the main collagen fiber that constitutes stromal components.

This collagen is known to decrease with age, and is the main factor of losing resilience or elasticity of skin, making wrinkles and sagging. Therefore, many studies are actively made for protecting and maintaining collagen, in the beauty industry, etc.

Under such circumstances as in the above, almost no study on effect of plasmalogen on collagen in skin has been made up to now.

CITATION LIST

Non-Patent Literature

Non-Patent Literature 1: Fujino T. et al, "Efficacy and Blood Plasmalogen Changes by Oral Administration of Plasmalogen in Patients with Mild Alzheimer's Disease and Mild Cognitive Impairment: A Multicenter, Randomized, Double-blind, Placebo-controlled Trial" EBioMedicine, [17] (2017) 199-205

SUMMARY OF INVENTION

Technical Problem

The object of the present invention is to provide a composition having an excellent collagen production promoting effect.

Solution to Problem

The present inventors made a keen study to solve the above-mentioned object, and as a result, they found out that plasmalogen exerts an excellent effect on promoting collagen production, and completed the present invention. Spe-cifically, they found out that plasmalogen promotes phos-phorylation of human fibroblast cells, main cells constituting dermis, and of AMPK (AMP-activated protein kinase) of human hair outer root sheath cells to promote expression of COL1A1 (collagen type I alpha 1 chain) contributing to production of type I collagen representing 90% of skin collagen, and being present in dermis tissues, and as well to suppress expression of MMP1 being a gene promoting collagen degradation.

Specifically, the present invention relates to the following.

[1] A composition for ameliorating skin condition, com-prising plasmalogen.

[2] A composition for ameliorating skin resilience, com-prising plasmalogen.

[3] A composition for ameliorating skin wrinkles, com-prising plasmalogen.

[4] A composition for ameliorating skin sagging, com-prising plasmalogen.

[5] A composition for promoting collagen production, comprising plasmalogen.

[6] The composition according to any one of [1] to [5], wherein the plasmalogen is a plasmalogen extracted from an animal tissue.

[7] The composition according to [6], wherein the animal tissue is a tissue of an animal selected from shellfish, sea squirt, and birds.

[8] The composition according to [6] or [7], wherein the animal tissue is a tissue of scallops.

Advantageous Effects of Invention

The composition of the present invention has an excellent collagen production promoting effect.

BRIEF DESCRIPTION OF DRAWINGS

FIG. 5 shows the results showing the change in plasmalo-gen content with respect to the culture time in HDF-a cells treated with plasmalogen (PlsEtn).

FIG. 6 shows the results showing the change in content by type of plasmalogen (content of fatty acid constituting plasmalogen by type) with respect to the culture time in HDF-a cells treated with plasmalogen (PlsEtn).

FIG. 7 shows the results of COL1A1 mRNA expression of HDF-a cells, by the treatment of plasmalogen (PlsEtn).

DESCRIPTION OF EMBODIMENTS

Figure 1:
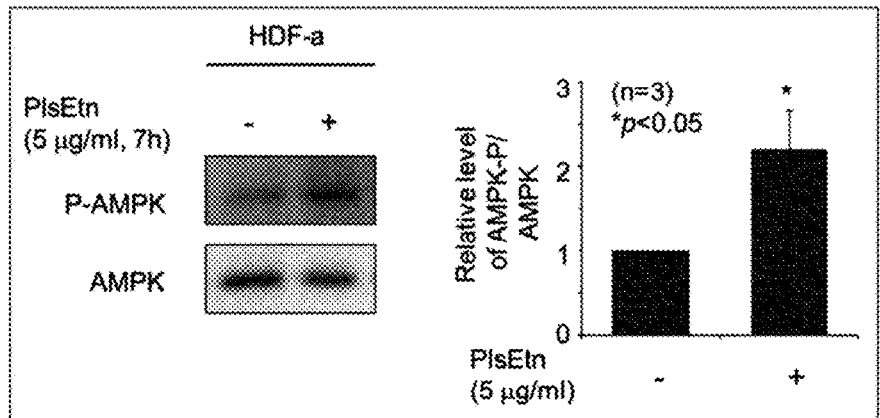
FIG. 1 shows the results of promotion of phosphorylation of AMPK (relative amount of Phospho-AMPK with respect to AMPK) in HDF-a cells (human adult fibroblast cells), by the treatment with plasmalogen (PlsEtn) (5 µg/mL, 7 hours).

The composition of the present invention is characterized by comprising plasmalogen.

The composition of the present invention promotes phosphorylation of AMPK of human fibroblast cells, etc. being main cells constituting dermis, promotes COL1A1 expression contributing to production of type I collagen, and suppresses MMP1 expression being collagen degradation promoting gene, to promote production of collagen, and thereby prompts recovery of skin condition that has degraded by the influence of age, or ultraviolet rays, etc., or maintenance of skin condition.

Specifically, the composition comprising plasmalogen of the present invention can be used as a composition for activating AMPK, a composition for promoting collagen production, or a composition for ameliorating skin condition. Here, as for amelioration of skin condition in the present invention, specific examples include suppressing decrease (maintenance) and/or improving skin resilience (elasticity), suppressing increase and/or decreasing skin wrinkles, suppressing and/or decreasing skin sagging, etc. Therefore, the composition of the present invention can be used as a composition for improving skin resilience, a composition for ameliorating skin wrinkles, or a composition for ameliorating skin sagging.

Plasmalogen used in the present invention is one type of phospholipid having an antioxidant effect, and is one of glycerophospholipid. It is a unique subclass of glycerophospholipid characterized by having a vinyl-ether linkage in the sn-1 position of glycerol backbone. It is observed at a high concentration in cell membrane in tissues of many mammals. As plasmalogen, those having a fatty acid ester linkage in the sn-2 position is preferable.

The plasmalogen used in the present invention is not particularly limited as long it is generally classified as plasmalogen, and examples include choline plasmalogen, ethanolamine plasmalogen, inositol plasmalogen, and serine plasmalogen. Among these, choline plasmalogen and ethanolamine plasmalogen are preferable, and ethanolamine plasmalogen is particularly preferable.

The plasmalogen of the present invention can be extracted from animal tissues. Animal tissues are not particularly limited as long it comprises plasmalogen, and examples include aquatic animals such as shellfish, sea squirt, sea cucumber, salmon, skipper and bonito, and birds. Among these, shellfish, sea squirt, and birds are preferable, and shellfish are particularly preferable. As parts to be used, edible part (part that can be eat) is preferable. These animal tissues can be cut products, but it is preferable to use ground products since plasmalogen can be extracted more efficiently.

Examples of shellfish include edible clams such as scallops, mussels, and abalone, and snails, and scallops are particularly preferable. Scallops are edible clams belonging to Pectinidae, and for example, those belonging to the genus *Mizuhopecten*, and the genus *Pecten* can be exemplified. Specifically, common scallop (scientific name: *Mizuhopecten yessoensis*) collected in Japan, or European scallop (scientific name: *Pecten* maximus (Linnaeus)) collected in Europe can be exemplified. As edible parts, scallop eye and strings can be exemplified.

Sea squirts are edible chordates belonging to Pyuridaethe, and those belonging to the genus *Haloncynthia*, the genus *Halocynthia aurantium* can be exemplified. Specifically, *Maboya* (scientific name: *Haloncynthia roretzi*) and Akaboya (scientific name: *Halocynthia aurantium*) can be exemplified. As edible parts, meats (fascia) can be exemplified.

Birds are not particularly limited as long as it is edible birds, and for example, chicken, silky fowl and canard can be exemplified. As edible parts, breast meat comprising plasmalogen in abundance is preferable.

Extraction of plasmalogen can be performed by using water, organic solvent, and water-containing organic solvent, and it is preferable to perform enzyme treatment in combination. For example, ethanol extraction method, and hexane extraction method can be exemplified, and ethanol extraction method is preferable.

Ethanol extraction method is not particularly limited as long it is a method of extracting using ethanol (including water-containing ethanol), and examples include methods described in Japanese published unexamined application No. 2019-140919, Japanese published unexamined application No. 2018-130130, Republished patent No. 2012-039472, Japanese published unexamined application No. 2010-065167, and Japanese published unexamined application No. 2010-063406, etc.

Hexane extraction method is not particularly limited as long as it is a method of extracting using hexane, and examples include methods described in Republished patent No. 2009-154309, Republished Patent No. 2008-146942, etc.

The composition of the present invention can be used as an oral agent or a parenteral agent. As for a parental agent, examples include external agent and injection agent. The external agent is not particularly limited as long as it can applied to skin, scalp, etc. Example of its form include skin external agent such as ointment, cream, gel, lotion, emulsion, pack, poultice, etc.

Further, when using as an oral agent, examples of its form include, for example, tablet form, capsule form, powder form, granule form, liquid form, grain form, bar form, plate form, block form, solid form, pellet form, paste form, cream form, caplet form, gel form, chewable form, stick form, or the like. Among these, capsule form is preferable.

The composition for ameliorating skin condition, etc. of the present invention is not particularly limited as long as it can be distinguished from other products as product, in the point of comprising plasmalogen, and being used for ameliorating skin condition, etc., and examples include medicine (including quasi-drug), cosmetics, or as so-called health food products such as functional foods which indication of efficacy is allowed from a prescribed authority, including foods for specified health use, foods with nutrient function claims, foods with function claims, or the like. Further, those with an indication of having skin condition ameliorating effect (effect related to resilience, wrinkles, sagging) on any of the main body, package, instructions, advertisement of the product of the present invention are encompassed in the scope of the present invention. Further, since skin condition is ameliorated by promoting collagen production, those indicating collagen production promotion are also encompassed in the scope of the present invention.

For example, in cosmetics or health foods, it can be indicated specifically as "maintaining skin resilience", "preventing wrinkles or sagging", "to those who are worried about skin aging", etc.

As for the content of plasmalogen in the composition of the present invention, it can be appropriately comprised within the scope with which the effect is exerted. It depends on the form, but for example it is preferable that plasmalogen is $10^{-10}\%$ by mass or more of the whole composition of the present invention, in terms of dry mass equivalent, more preferable to be $10^{-5}\%$ by mass or more, further preferable to be 0.1% by mass or more, and particularly preferable to be 1.0% by mass or more.

The amount of intake in case where the composition of the present invention is an oral agent is not particularly limited. However, from the viewpoint to more significantly exert the effect of the present invention, it is preferable to intake so that the amount of intake of plasmalogen of an adult per day is $10^{-6}$ μg or more per day, more preferable so that it is 1 μg or more per day, further preferable so that it is 500 μg or more per day, and particularly preferable so that it is 1000 μg or more per day. The upper limit is for example 20,000 μg per day, and preferably 10,000 μg per day.

The composition of the present invention can be stored in one container, or for example in plural containers of 2 to 3, so that the amount of intake per day becomes the above-mentioned amount of intake, for one day.

The composition of the present invention can be produced by known production methods by adding ingredients other than active ingredients (plasmalogen) acceptable as oral agent, external agent or injection agent, according to need.

Examples of other ingredients other than active ingredients of the present invention include, for example, vitamin, mineral, protein, peptide, amino acid, animal oil, vegetable oil.

In the following, the present invention will be explained in detail, based on Examples.

Example 1

The effect of plasmalogen being the active ingredient of the composition of the present invention on skin was confirmed by using HDF-a cells (human fibroblast cells) and HHORSC cells (human hair outer root sheath cells) was confirmed.

[Ethanolamine Plasmalogen (PlsEtn)]

As Ethanolamine plasmalogen, one prepared by extracting common scallop (scientific name: *Mizuhopecten yessoensis*) with ethanol, and purified with HPLC was used.

[Cell Culture]

As human fibroblast cells, Human Dermal Fibroblasts-adult (HDF-a) cells (#2320) were used, and as human hair outer root sheath cells, Human Hair Outer Root Sheath (HHORSC) cells (#2420) were used. Those cells were purchased from ScienCell Research Laboratories. HDF-a cells were cultured in Fibroblast Medium (FM, #2301), and HHORSC cells were cultured in Mesenchymal Stem Cell Medium (MSCM, #7501). Cells up to 10 passages were used in the experiment.

HDF-a cells cultured from the previous day were cultured for a predetermined time (3 hours or 7 hours) in a mixed medium of 900 μL of FM and 100 μL of PLsEtn solution in which PlsEtn (0.5 μg or 5 μg) was previously suspended by ultrasonic treatment in Opti-MEM™ Reduced Serum Medium (ThemoFisher, #22600050).

HHORSC cells were also similarly cultured in the presence of 5 μg/ml of PlsEtn for 7 hours, except using MSCM instead of FM. As control, cells (HDF-a cells and HHORSC cell) cultured in a medium of the same composition not containing PlsEtn were used.

Further, except of using phosphatidylethanolamine (PtdEtn) extracted from soybean instead of PlsEtn, HDF-a cells were similarly cultured for 3 hours in the presence of 0.5 μg/ml PtdEtn.

Cells were washed with phosphate buffer solution (PBS) and collected. RNA expression level was detected after storing the washed cells in a culture ultra-low temperature freezer.

[Analysis of Phosphorylation of AMPK]

HDF-a cells were collected with Buffer A (0.25 M sucrose, 10 mM Hepes-KOH, pH 7.5, 1 mM EDTA, protease inhibitor cocktail) and centrifuged. The obtained cells were suspended in Buffer A, crushed by ultrasonic treatment, and after protein determination, the same protein amount was subjected to electrophoresis. Next, the resultant was transferred on PVDF membrane, and detected by western blotting using Phospho-AMPK a (Thr172) antibody (Cell Signaling technology, #2535S) and AMPK a antibody (Cell Signaling technology, #58315). The signal was determined by Multi Gauge software version 3.0 software (Fuji Film). The signal obtained with Phospho-AMPK a (Thr172) antibody was divided by the signal obtained with AMPK a antibody for standardization. Further, the level obtained from untreated cells was set as 1, to show the signal strength in cells having undergone each treatment as a relative value. It was tried 3 times or more, and the mean level and standard deviation were shown.

HHORSC cells were analyzed by the same manner.

Figure 2:
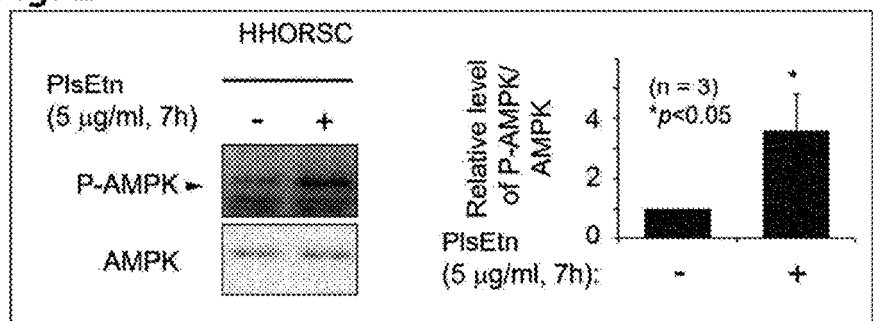
FIG. 2 shows the results of promotion of phosphorylation of AMPK (relative amount of Phospho-AMPK with respect to AMPK) in HHORSC cells (human hair outer root sheath cells), by the treatment with plasmalogen (PlsEtn) (5 µg/mL, 7 hours).
Figure 3:
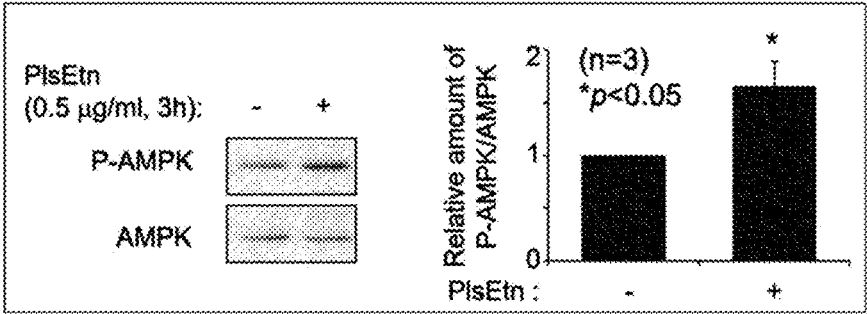
FIG. 3 shows the results of promotion of phosphorylation of AMPK (relative amount of Phospho-AMPK with respect to AMPK) in HDF-a cells (human fibroblast cells), by the treatment with plasmalogen (PlsEtn) (0.5 µg/mL, 3 hours).
Figure 4:
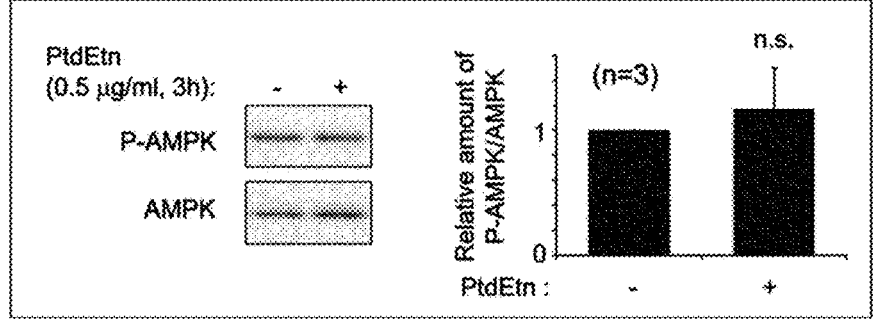
FIG. 4 shows the results of promotion of phosphorylation of AMPK (relative amount of Phospho-AMPK with respect to AMPK) in HDF-a cells (human fibroblast cells), by the treatment with phosphatidylethanolamine extracted from soybean (PtdEtn) (0.5 µg/mL, 3 hours).

FIG. 1 shows the results of promotion of phosphorylation of AMPK (relative amount of Phospho-AMPK with respect to AMPK) in HDF-a cells cultured for 7 hours in the presence of 5 μg/mL of PlsEtn. FIG. 2 shows the results of promotion of phosphorylation of AMPK (relative amount of Phospho-AMPK with respect to AMPK) in HHORSC cells cultured for 7 hours in the presence of 5 μg/mL of PlsEtn. Further, FIG. 3 shows the results of promotion of phosphorylation of AMPK (relative amount of Phospho-AMPK with respect to AMPK) in HDF-a cells cultured for 3 hours in the presence of 0.5 μg/mL of PlsEtn. FIG. 4 shows the results of promotion of phosphorylation of AMPK (relative amount of Phospho-AMPK with respect to AMPK) in HDF-a cells cultured for 3 hours in the presence of 0.5 μg/mL of PtdEtn extracted from soybean.

As shown in FIG. 1, in HDF-a cells cultured for 7 hours in the presence of 5 μg/mL of PlsEtn, phosphorylation of AMPKα essential for AMPK activation was enhanced as compared to cells cultured in the absence of PlsEtn. Further, as shown in FIG. 2, in HHORSC cells, similar results as for HDF-a cells were obtained.

From the above results, it can be thought that PlsEtn has an action of promoting phosphorylation of AMPK in various cells, including HDF-a cells and HHORSC cells.

Further, as shown in FIG. 3, in HDF-a cells cultured for 3 hours in the presence of 0.5 μg/mL of PlsEtn, enhancement of phosphorylation of AMPK was observed, while as shown in FIG. 4, phosphorylation of AMPK was not observed in the presence of 0.5 μg/mL of PtdEtn.

[Measurement of Change in PlsEtn Content in Cells]

Plasmalogen content and its type in HDF-a cells cultured in the presence of PlsEtn were confirmed.

FIG. 5 shows the measurement results of plasmalogen content in HDF-a cells with respect to the culture time. Further, FIG. 6 shows the measurement results of content by type of plasmalogen (content by type of fatty acid constituting plasmalogen) in HDF-a cells with respect to the culture time.

As shown in FIG. 5 and FIG. 6, when culturing in the presence of 0.5 μg/mL of PlsEtn, there was no change in the total amount of plasmalogen in HDF-a cells, and the plasmalogen level having C16:0, C18:0, or C18:1 fatty acid alcohol.

From the above results, it can be inferred that PlsEtn functions as a ligand against non-identified receptor, and promotes phosphorylation of AMPK, and not the change of level or quality of PlsEtn of HDF-a cells.

[Quantification of COL1A1 and MMP1 mRNA in HDF-a Cells]

Enhancement of phosphorylation of AMPK (AMP-activated protein kinase) promotes synthesis of nicotinamide adenine dinucleotide (NAD) depending on nicotinamide phosphoribosyltransferase (NAMPT) which is a rate-limiting enzyme of NAD synthesis. As a result, activation of NAD dependent deacetylase sirtuin (Sirt1) having NAD as substrate is expected. Thus, gene expression of COL1A1 encoding one of constituting protein of Sirt1 dependent type I collagen, and of MMP1 encoding matrix metalloproteinase-1 being a collagen-degrading enzyme were detected.

HDF-a cells were cultured for 7 hours as stated above, and RNA was extracted using TRIzol. Then, 1st strand cDNA was adjusted by using PrimeScript RT Master Mix, and mRNA expression of the target gene and endogenous control gene was detected by real time PCR, with Mx3000P QPCR (Stratagene) by using TB Green Premix Ex Taq II. Trials were performed 3 times or more. Besides COL1A1 and MMP1 being target genes, 18S ribosomal RNA (18S rRNA) was selected as endogenous control gene. Primers for detecting mRNA of each gene are as follows.

```
COL1A1 1184Fw:
5'-GTGCTAAAGGTGCCAATGGT-3',

COL1A1 1311Rv:
5'-ACCAGGTTCACCGCTGTTAC-3',

MMP1 141Fw:
5'-TGGGAGGCAAGTTGAAAAGC-3',

MMP1 275Rv:
5'-CATCTGGGCTGCTTCATCAC-3', 18S rRNA Fw:
5'-AGTCCCTGCCCTTTGTACACA-3'

18S rRNA Rv:
5'-CGATCCGAGGGCCTCACTA-3'
```

Figure 8:
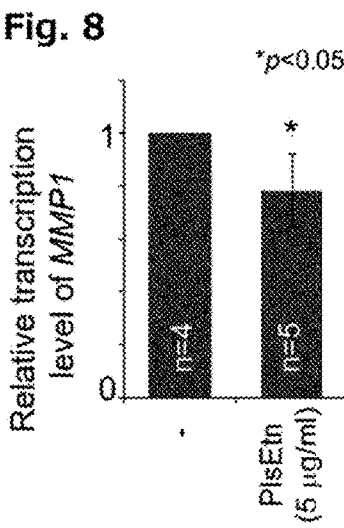
FIG. 8 shows the results of mRNA expression of MMP1 which is a collagen degradation promoting gene of HDF-a cells, by the treatment of plasmalogen (PlsEtn).

FIG. 7 shows the expression results of COL1A1 mRNA expression of HDF-a cells. FIG. 8 shows the results of mRNA expression of MMP1 of HDF-a cells.

As shown in FIG. 7 and FIG. 8, as compared with control not added with PlsEtn, in the presence of PlsEtn, expression of COL1A1 was promoted and expression of MMP1 was suppressed. Therefore, it can be thought that PlsEtn promotes collagen production in skin, and can prompt amelioration of skin condition.

[Quantification of COL1A1 mRNA in HDF-a Cells]

As ethanolamine plasmalogen (PlsEtn), those extracted from scallop, similarly as in the above, and those extracted from mussel (scientific name: Mytilus Linnaeus) similarly as from scallop with ethanol and purified with HPLC were used.

Culture of HDF-a cells, extraction of RNA and real time PCR were performed by the same method as above.

Figure 9:
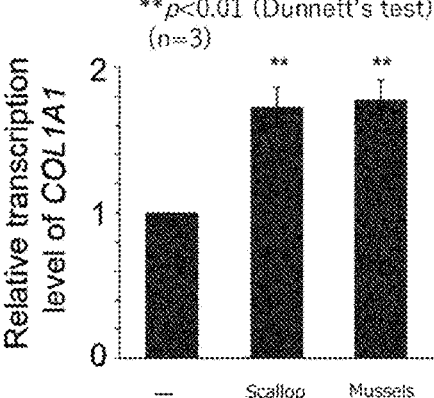
FIG. 9 shows the results of COL1A1 mRNA expression of HDF-a cells, by the treatment of plasmalogen (PlsEtn).

FIG. 9 shows the results of COL1A1 mRNA expression of HDF-a cells, by PlsEtn derived from scallop and mussel. In case of adding PlsEtn extracted from both tissues, COL1A1 expression was promoted as compared to control not added with PlsEtn.

[Quantification of COL1A1 mRNA in Mouse Skin]

In mouse skin applied with plasmalogen, expression of COL1A1 was detected.

7 weeks-old male C3H mice were used. Mice were preliminary bread. Body hair on the dorsal skin was shaved at the age of 8 weeks-old with an electric hair clipper for animals and depilated with depilatory cream. From 48 hours after shaving, application of 70% EtOH solution containing 10 mg/ml PlsEtn (derived from scallop) was started. Frequency of application was 5 times/week for 4 weeks, and the quantity of application was 20 μl/cm². Further, as control, 70% EtOH solution not containing plasmalogen was applied at the same frequency and quantity of application. There were 3 mice in each treatment section.

From after 4 weeks, skin pieces of applied parts obtained from control and from mice applied with 10 mg/ml PlsEtn were made into small pieces with scissors, and RNA was extracted by using TRIzol. Then, 1st strand cDNA was adjusted by using PrimeScript RT Master Mix. Then, mRNA expression of COL1A1 being the target gene, and of GAPDH being the endogenous control gene was detected by real time PCR by using TB Green Premix Ex Taq II with ABI 7500 (Applied Biosystems). Primers for detecting mRNA of each gene are as follows.

```
MmCOL1A1 2818Fw:
5'-cctcagggtattgctggaca-3',

MmCOL1A1 2930Rv:
5'-gaaggaccttgtttgccagg-3',

MmGAPDH qRTFw:
5'-tggtgaaggtcggtgtgaac-3',

MmGAPDH qRTRv:
5'-caatgaaggggtcgttgatgg-3'
```

Figure 10:
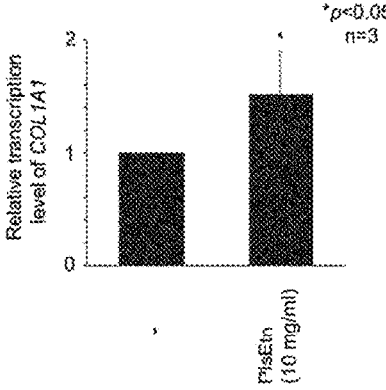
FIG. 10 shows the results of COL1A1 mRNA expression of HDF-a cells in mouse skin, by the treatment of plasmalogen (PlsEtn).

FIG. 10 shows the results of COL1A1 mRNA expression in mouse.

As shown in FIG. 10, as compared to control not added with PlsEtn, in the presence of PlsEtn, COL1A1 expression was promoted. Therefore, it can be thought that PlsEtn promotes collagen production in skin, and can prompt amelioration of skin condition.

[Verification of Effect of Plasmalogen in Human Skin]

Effect in human skin by oral intake of plasmalogen was verified.

To 9 female subjects in the age of 20s to 80s, who are worried about their damaged skin, 2 to 4 granules per day of tablets containing scallop derived plasmalogen (0.5 mg) were administered. The subjects had a questionnaire about the change after plasmalogen intake with respect to skin condition before intake. The questionnaire was made by the following evaluation on a scale of 1 to 5.

Score 5: ameliorated considerably
Score 4: ameliorated a little
Score 3: no change
Score 2: worsened a little
Score 1: worsened considerably Table 1 shows the results of the questionnaire about the change in skin condition by intake of plasmalogen.

TABLE 1

| Case | Age | Dosing period | Skin condition before intake | Evaluation score after intake |
|---|---|---|---|---|
| 1 | 20s | 12 months | Oily skin, dry skin, skin damage, itchiness of skin (redness), acne (pimple), wrinkle (small line), skin damage due to masks, somberness | 4 |
| 2 | 50s | 3 years | Dry skin (drying around eyes in spring) | 4 |
| 3 | 50s | 2 years and 6 months | Dry skin, roughness on skin besides face (chapped lips on winter, cracking on fingertip (next to nail), chapped skin on the back of hand) | 5 |
| 4 | 80s | 3 months | Dry skin | 5 |
| 5 | 60s | 3 years | Tend to be dry | 5 |

As shown in Table 1, among the test subjects having intake plasmalogen, more than a half answered "score 5: ameliorated considerably", or "score 4: ameliorated a little". There was no test subject having answered "score 2: worsened a little", or "score 1: worsened considerably".

Therefore, it has been revealed that by orally intaking plasmalogen, skin condition can be ameliorated.

Example 2

Formulation Example 1

Skin lotion (100 g) was produced according to the following formulation.

| | |
|---|---|
| Scallop extracted plasmalogen | 0.5 mg |
| Glycerin | 0.5 mg |
| Purified water | remaining part |

Formulation Example 2

A hard capsule agent was produced according to the following formulation.

| | |
|---|---|
| Scallop extracted plasmalogen | 0.5 mg |
| Cytrodextrin | 3.3 mg |
| Amino acids | 1.2 mg |
| Pine-Dex | 185.0 mg |

INDUSTRIAL APPLICABILITY

Since the composition of the present invention can be used as an external agent or oral agent, it is industrially useful.

The invention claimed is:

1. A method for ameliorating dry skin, comprising administering a composition comprising plasmalogen to a human having dry skin.

2. The method according to claim 1, wherein the plasmalogen is a plasmalogen extracted from an animal tissue.

3. The method according to claim 1, wherein the administration is oral administration.

* * * * *